US010179179B2

United States Patent
Cheng et al.

(10) Patent No.: US 10,179,179 B2
(45) Date of Patent: Jan. 15, 2019

(54) MAGNETIC NANOPARTICLES FOR DISEASE DIAGNOSTICS

(71) Applicant: Nano and Advanced Materials Institute Limited, Hong Kong (HK)

(72) Inventors: Kwok Kin Cheng, Hong Kong (HK); Sau Kuen Connie Kwok, Hong Kong (HK); Chun Hay Ko, Hong Kong (HK); Kevin Tsai, Hong Kong (HK); Chun Fai Ng, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 0 days.

(21) Appl. No.: 15/789,012

(22) Filed: Oct. 20, 2017

(65) Prior Publication Data

US 2018/0117185 A1  May 3, 2018

Related U.S. Application Data

(60) Provisional application No. 62/496,757, filed on Oct. 28, 2016.

(51) Int. Cl.
*A61K 9/00* (2006.01)
*A61K 49/18* (2006.01)
*A61K 49/10* (2006.01)

(52) U.S. Cl.
CPC .......... *A61K 49/186* (2013.01); *A61K 49/106* (2013.01)

(58) Field of Classification Search
CPC ................................................. A61K 49/186
See application file for complete search history.

(56) References Cited

U.S. PATENT DOCUMENTS

2016/0250612 A1* 9/2016 Oldenburg .............. C01B 33/18
428/404

OTHER PUBLICATIONS

Yang et al.; Detection of Amyloid Plaques Targeted by USPIO-Aβ1-42 in Alzheimer's Disease Transgenic Mice Using Magnetic Resonance Microimaging; NeuroImage; 2011; pp. 1600-1609; vol. 55, Issue 4; Elsevier.
Ren et al.; Preparation and Therapeutic Efficacy of Polysorbate-80-Coated Amphotericin B/PLA-b-PEG Nanoparticles; Journal of Biomaterials Science, Polymer Edition; 2009; pp. 1369-1380; vol. 20, Issue 10; Koninklijke Brill NV.
Sigurdsson et al.; A Non-Toxic Ligand for Voxel-Based MRI Analysis of Plaques in AD Transgenic Mice; Neurobiology of Aging; 2008; pp. 836-847; vol. 29, Issue 6; Elsevier.
Liu et al.; Mixing in a Multi-Inlet Vortex Mixer (MIVM) for Flash Nano-Precipitation; Chemical Engineering Science; 2008; pp. 2829-2842; vol. 63, Issue 11; Elsevier.
Gavi et al.; CFD modelling and scale-up of Confined Impinging Jet Reactors; Chemical Engineering Science; 2007; pp. 2228-2241; vol. 62, Issue 8; Elsevier.
Gavi et al.; CFD Modelling of Nano-Particle Precipitation in Confined Impinging Jet Reactors; Chemical Engineering Research and Design; 2007; pp. 735-744; vol. 85, Issue 5; Institution of Chemical Engineers.

(Continued)

*Primary Examiner* — Paul W Dickinson
(74) *Attorney, Agent, or Firm* — Spruson & Ferguson (Hong Kong) Limited

(57) ABSTRACT

Provided herein is a nanoparticle comprising a metal core and a polymer shell coating the metal core useful as a magnetic resonance contrast agent.

20 Claims, 17 Drawing Sheets

(56) References Cited

OTHER PUBLICATIONS

Chang et al.; Using Nanoscale Zero-Valent Iron for the Remediation of Polycyclic Aromatic Hydrocarbons Contaminated Soil; Journal of the Air & Waste Management Association; 2005; pp. 1200-1207; vol. 55, Issue 8; Air & Waste Management Association.

Sun et al.; Specific Role of Polysorbate 80 Coating on the Targeting of Nanoparticles to the Brain; Biomaterials; 2004; pp. 3065-3071; vol. 25, Issue 15; Elsevier.

Wadghiri et al.; Detection of Alzheimer's Amyloid in Transgenic Mice Using Magnetic Resonance Microimaging; Magnetic Resonance in Medicine; 2003; pp. 293-302; vol. 50, Issue 2; Wiley.

* cited by examiner

| PVP % | Injection Rate (mL/min) | Size and PDI |
|---|---|---|
| 0.8 | 45/5 | Initial ~120nm, precipitate after 45min (>3000nm) |
| 1.5 | 45/5 | Size: 116.2±4.6nm<br>PDI: 0.159±0.015 |
| 3 | 45/5 | Size: 88.2±5.2nm<br>PDI: 0.195±0.009 |
| 3 | 90/10 | Size: 70.5±1.7nm<br>PDI: 0.176±0.020 |

FIG. 7

MAGNETIC NANOPARTICLES FOR DISEASE DIAGNOSTICS

CROSS REFERENCE TO RELATED APPLICATION

The present application claims benefits from U.S. provisional patent application Ser. No. 62/496,757 filed Oct. 28, 2016, and the disclosure of which is incorporated herein by reference in their entirety.

FIELD OF THE INVENTION

The present disclosure relates to magnetic nanoparticles useful as magnetic resonance imaging contrast agents, formulations thereof, and methods for producing thereof.

BACKGROUND OF THE INVENTION

Conventional in vivo active targeting diagnostic agents commonly rely on a specific peptide or antibody, which is capable of specifically binding the target of interest, linked to a signaling agent. However, these diagnostic agents can be disadvantaged by toxicity of the conjugated peptides or antibodies and their large molecular weight may inhibit the penetration of such targeting agents through biological barriers, such as blood-brain barrier, small intestine, nasal, skin and mouth mucosa. The blood-brain barrier is one of the most stringent barriers in the human body and prevents most foreign materials from passing through. The blood brain barrier can thus severely limit the choice of diagnostic agents for neuronal diseases. The most common methods for neuronal disease diagnosis are positron emission tomography (PET) and computer tomography (CT) scans. However, these approaches are complicated and expose patients to radiation, which may increase the risk of continuous disease monitoring. In order to provide safer and longer term disease diagnosis and monitoring, new diagnostic platform technologies are needed.

Magnetic resonance imaging (MRI) is an alternative imaging technique, which is widely used in clinical settings. MRI uses magnetic fields and radio waves to generate images of the target tissue or organs in the body. Since MRI does not utilize X-rays or positron emitting radioisotopes, it is considered safer than CT and PET.

While MRI of anatomical structures and blood flow can be imaged directly, due to their natural contrast, other tissue types require the use of an MRI contrast agent for imaging. The most common MRI contrast agents are based on chelates of gadolinium. Iron- and manganese-based MRI contrast agents have also been evaluated.

MRI contrast agents, and in particular iron-based MRI contrast agents, are susceptible agglomeration and exhibit poor in vivo distribution and half-life. MRI contrast agents are typically coated with biocompatible polymers to prevent such agglomeration and to improve their in vivo distribution.

Another method for improving targeted localization of MRI contrast agents is by using targeting agents that selectively bind to the target organ or tissue of interest and also has the ability to improve the relaxivity of the contrast agent, which can also increases the magnetic resonance signal.

Notwithstanding the foregoing, there is still a need for new MRI contrast agents with improved stability and pharmacokinetics.

SUMMARY OF THE INVENTION

The present disclosure provides magnetic nanoparticles having improved long term stability, improved pharmacokinetics, ability to penetrate the blood brain barrier, and long circulation half life with reduced toxic effects on the patient.

In a first aspect provided herein is a nanoparticle comprising a metal core and a polymer shell coating the metal core, wherein the polymer shell comprises an inner shell comprising a first polymer and an outer shell comprising a second polymer, wherein the first polymer comprises a polyethylene glycol: polylactic acid coblock polymer (PEG-PLA) or a polyethylene glycol: poly(lactic-co-glycolic acid) coblock polymer (PEG: PLGA) and the second polymer is polyvinylpyrrolidone (PVP), polyvinyl alcohol (PVA), a polyamide, or a combination thereof and the mass ratio of the metal core to the first polymer to the second polymer is about 1:0.25:3 to about 1:4:4.

In a first embodiment of the first aspect provided herein is a nanoparticle, wherein the metal core comprises Fe, Gd, Mn, Sn, Zn, Cu, Mg, or Pt.

In a second embodiment of the first aspect provided herein is a nanoparticle, wherein the metal core comprises a metal flavonoid salt, a metal curcumonoid salt or a metal dye salt, wherein the metal is Fe, Gd, Mn, Sn, Zn, Cu, Mg, or Pt.

In a third embodiment of the first aspect provided herein is a nanoparticle, wherein the metal curcumonoid salt comprises curcumin, demethoxycurcumin, or bismthoxycurcumin and the metal dye salt comprises disodium 4-amino-3-[4-[4-(1-amino-4-sulfonato-naphthalen-2-yl)diazenylphenyl]phenyl]diazenyl-naphthalene-1-sulfonate, Thioflavin T, or Thioflavin S.

In a fourth embodiment of the first aspect provided herein is a nanoparticle, wherein the metal core comprises Fe, Gd, Mn, or Sn.

In a fifth embodiment of the first aspect provided herein is a nanoparticle, wherein the metal core comprises $FeO_3$, a core-shell $Fe(0)@Fe_3O_4$, or $Fe(Cur)_3$.

In a sixth embodiment of the first aspect provided herein is a nanoparticle, wherein the first polymer is PEG-PLA comprising a polyethylene glycol block having an average molecular weight of 1,000 to 15,000 amu and a polylactic acid block having an average molecular weight of 1,000 to 15,000 amu.

In a seventh embodiment of the first aspect provided herein is a nanoparticle, wherein the metal curcumonoid salt comprises curcumin, demethoxycurcumin, or bismthoxycurcumin and the metal dye salt comprises disodium 4-amino-3-[4-[4-(1-amino-4-sulfonato-naphthalen-2-yl)diazenylphenyl]phenyl]diazenyl-naphthalene-1-sulfonate, Thioflavin T, or Thioflavin S and the first polymer is PEG-PLA comprising a polyethylene glycol block having an average molecular weight of 1,000 to 3,000 amu and a polylactic acid block having an average molecular weight of 7,000 to 10,000 amu.

In a eighth embodiment of the first aspect provided herein is a nanoparticle, wherein the first polymer is PEG: PLGA comprising a polyethylene glycol block having an average molecular weight of 1,000 to 15,000 amu and poly(lactic-co-glycolic acid) block having an average molecular weight of 1,000 to 15,000 amu.

In a ninth embodiment of the first aspect provided herein is a nanoparticle, wherein the first polymer is PEG: PLGA comprising a polyethylene glycol block having an average molecular weight of 1,000 to 15,000 amu and the poly(lactic-co-glycolic acid) block having an average molecular weight of 1,000 to 15,000 amu and the second polymer is PVP having an average molecular weight of 12,000 to 30,000.

In a tenth embodiment of the first aspect provided herein is a nanoparticle, wherein the first polymer is PEG: PLGA comprising a polyethylene glycol block having an average molecular weight of 1,000 to 15,000 amu and the poly (lactic-co-glycolic acid) block having an average molecular weight of 1,000 to 15,000 amu; the second polymer is PVP having an average molecular weight of 12,000 to 30,000; the metal core comprises Fe(Cur)$_3$; and the mass ratio of the metal core to the first polymer to the second polymer is about 1:0.5:3.4 to about 1:3:3.8.

In an eleventh embodiment of the first aspect provided herein is a nanoparticle, wherein the first polymer is PEG: PLGA comprising a polyethylene glycol block having an average molecular weight of 1,000 to 15,000 amu and the poly(lactic-co-glycolic acid) block having an average molecular weight of 1,000 to 15,000 amu; the second polymer is PVP having an average molecular weight of 12,000 to 30,000; the metal core comprises Fe(Cur)$_3$ and the mass ratio of the metal core to the first polymer to the second polymer is about 1:0.5:3.4 to about 1:3:3.8; and the first polymer is PEG-PLA comprising a polyethylene glycol block having an average molecular weight of 2,000 amu and a polylactic acid block having an average molecular weight of 10,000 amu.

In a twelfth embodiment of the first aspect provided herein is a nanoparticle, wherein the first polymer is PEG: PLGA comprising a polyethylene glycol block having an average molecular weight of 1,000 to 15,000 amu and poly(lactic-co-glycolic acid) block having an average molecular weight of 1,000 to 15,000 amu; the second polymer is PVP having an average molecular weight of 12,000 to 30,000; the metal core comprises Fe(Cur)$_3$; the mass ratio of the metal core to the first polymer to the second polymer is about 1:0.5:3.4 to about 1:3:3.8; the first polymer is PEG-PLA comprising a polyethylene glycol block having an average molecular weight of 2,000 amu and a polylactic acid block having an average molecular weight of 10,000 amu; and the average hydrodynamic diameter of the nanoparticle is about 10 nm to about 300 nm.

In a second aspect provided herein is pharmaceutical composition comprising a diagnostically effective amount of a nanoparticle of the first aspect and at least one pharmaceutically acceptable excipient.

In a third aspect provided herein is a method of performing a magnetic resonance imaging diagnostic procedure comprising the steps of:
a. administering to a subject a diagnostically effective amount of a nanoparticle of the first aspect; and
b. exposing the subject to a magnetic resonance imaging procedure, thereby generating an image of at least a portion of the body of the subject.

In a first embodiment of the third aspect provided herein is a method, wherein the nanoparticle comprises a metal flavonoid salt that binds to amyloid plaques in the subject.

In a second embodiment of the third aspect provided herein is a method, wherein the method further comprises the step of processing the image of at least a portion of the body of the subject to diagnose the presence or absence of Alzheimer's disease, Huntington's disease, mad cow disease, multiple sclerosis, Parkinson's disease, Lewy body dementia, or stroke.

In a third embodiment of the third aspect provided herein is a method, wherein the nanoparticle comprises a metal flavonoid salt that binds to amyloid plaques in the subject and the at least a portion of the body of the subject comprises the brain.

In a fourth embodiment of the third aspect provided herein is a method, wherein the subject is a human.

In a fifth embodiment of the third aspect provided herein is a method, wherein the nanoparticle of the first of the first aspect is administered parentally.

BRIEF DESCRIPTION OF THE DRAWINGS

Embodiments of the present invention are described in more detail hereinafter with reference to the drawings, in which:

FIG. 7 shows the effect of PVP concentration (w/v) and injection rate on the size and polydispersity index of the iron-curcumin complex nanoparticles prepared by MIVM in Example 2 below.

DETAILED DESCRIPTION OF PREFERRED EMBODIMENTS

Figure 1A:
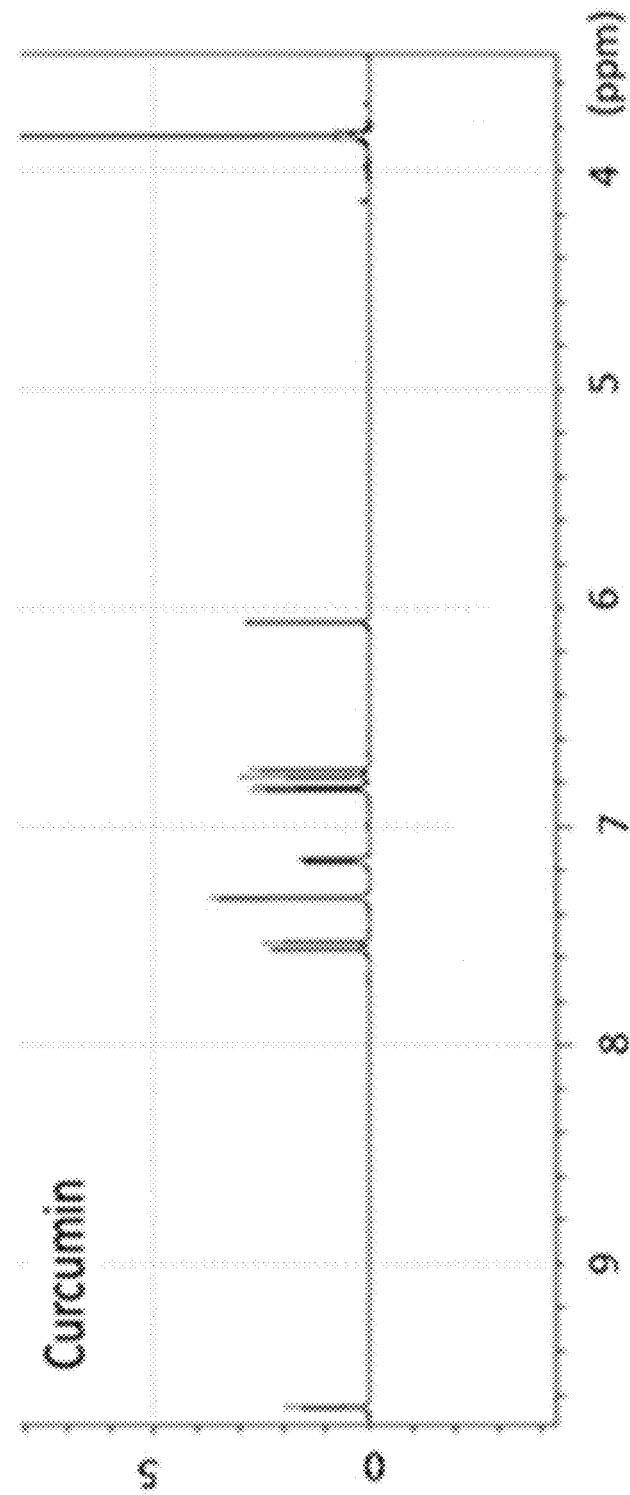
FIG. 1A shows the $^1$H-NMR of curcumin.

In the following description, examples and/or specific embodiments are set forth as preferred examples. It will be apparent to those skilled in the art that modifications, including additions and/or substitutions, may be made without departing from the scope and spirit of the disclosure.

The nanoparticles disclosed herein comprise a metal core. The metal core can be any metal that is capable of modifying the T1 and/or T2 relaxation time of, e.g., lipid and/or water protons. Examples of suitable metals include paramagnetic or superparamagnetic metals with the appropriate oxidation state selected from the group consisting of chromium, manganese, manganese, iron, cobalt, nickel, copper, praseodymium, neodymium, samarium, gadolinium, terbium, dysprosium, holmium, erbium, europium and ytterbium. Specific examples of such metals include, but are not limited to chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III).

In certain embodiments, the metal core comprises iron, gadolinium, manganese, tin, zinc, copper, magnesium, or platinum.

In instances where the metal core comprises gadolinium, the metal core can comprise gadolinium (III) chloride ($GdCl_3$) or gadolinium(III) nitrate ($Gd(NO_3)_3$).

In instances where the metal core comprises manganese, the metal core can comprise manganese chloride ($MnCl_3$) or manganese nitrate ($Mn(NO_3)_3$).

In certain embodiments, the metal core comprises a core-shell structure comprising an iron(0) core and a shell comprising $Fe_2O_3$, $Fe_3O_4$, or a combination thereof.

The metal core can further comprise targeting ligand, which enable the nanoparticle to localize to specific targets within the patient. The targeting ligand can be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, therapeutic agents, genetic material, including nucleosides, nucleotides and polynucleotides, curcuminoids, and flavonoids.

The term "target" or "target molecule" refers to any substance that a targeting ligand can bind to, such as proteins or polypeptides, cells, receptors, carbohydrates, lipids, etc.

Examples of suitable targets and targeting ligands are disclosed, for instance, in U.S. Pat. No. 6,139,819, which is herein incorporated by reference.

In certain embodiments, the targeting ligand is a flavonoid selected from the group consisting of flavanols (e.g., quercetin, kaempferol, myricetin, and isorhamnetin), flavones (e.g., luteolin and apigenin), flavanones (e.g., hesperetin, naringenin, and eriodictyol), flavan-3-ols (e.g., (+)-catechin, (+)-gallocatechin, (−)-epicatechin, (−)-epigallocatechin, (−)-epicatechin 3-gallate, (−)-epigallocatechin 3-gallate, theaflavin, theaflavin 3-gallate, theaflavin 3'-gallate, theaflavin 3,3' digallate, and thearubigins), and anthocyanidins (e.g., cyanidin, delphinidin, malvidin, pelargonidin, peonidin, and petunidin).

In certain embodiments, the targeting ligand is a curcuminoid selected from the group consisting of curcumin, bis-demethoxycurcumin, and demethoxycurcumin, bis-o-demethyl curcumin.

In certain embodiments, the metal core comprises an iron, manganese, or gadolinium curcumin salt. The metal cation can be in the +1, +2, or +3 oxidation state. The metal curcumin salt can be represented by the chemical structure below:

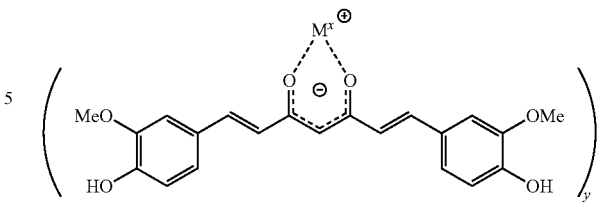

wherein,
M is iron, manganese, or gadolinium;
X is the oxidation state and is selected from +1, +2, or +3; and
Y represents the number of curcumin ligands bound to M and is equal in number to the oxidation state of M.

The metal core is coated by a polymer shell, wherein the polymer shell comprises an inner shell comprising a first polymer and an outer shell comprising a second polymer In certain embodiments, the first polymer is a polyethylene glycol: polylactic acid coblock polymer (PEG-PLA). The PEG-PLA can comprise a polyethylene glycol polymer block ranging from about 1,000 to about 15,000 average molecular weight (for example, from about 1,000 to about 15,000, about 1,000 to about 14,000, about 1,000 to about 13,000, about 1,000 to about 12,000, about 1,000 to about 11,000, about 1,000 to about 10,000, about 1,000 to about 9,000, about 1,000 to about 8,000, about 1,000 to about 7,000, about 1,000 to about 8,000, about 1,000 to about 7,000, about 1,000 to about 6,000, about 1,000 to about 5,000, about 1,000 to about 4,000 or about 2,000 to about 4,000 amu). In certain embodiments, the PEG-PLA comprises a polyethylene glycol block polymer having an average molecular weight of about 2,000 amu.

The PEG-PLA can comprise a polylactic acid polymer block ranging from 1,000 to 15,000 average molecular weight (for example, from about 1,000 to about 15,000, about 2,000 to about 15,000, about 3,000 to about 15,000, about 4,000 to about 15,000, about 5,000 to about 15,000, about 6,000 to about 15,000, about 7,000 to about 15,000, about 7,000 to about 14,000, about 7,000 to about 13,000, about 7,000 to about 12,000, about 7,000 to about 11,000, or about 7,000 to about 10,000 amu). In certain embodiments, the PEG-PLA comprises a polylactic acid block polymer having an average molecular weight of about 8,000 amu.

In certain embodiments, the second polymer is polyvinylpyrrolidone (PVP), polyvinyl alcohol (PVA), or a polyamide.

Examples of suitable PVP include those having an average molecular weight from about 10,000 to about 50,000. In some embodiments, the PVP has an average molecular weight of about 10,000 to about 30,000, about 12,000 to about 30,000, about 10,000 to about 20,000, or about 12,000 to about 20,000. In further embodiments, the PVP has a molecular weight of about 15,000 to about 20,000.

Examples of suitable PVA include those having an average molecular weight from about 10,000 to about 50,000. In some embodiments, the PVA has an average molecular weight of about 10,000 to about 30,000, about 12,000 to about 30,000, about 10,000 to about 20,000, or about 12,000 to about 20,000. In further embodiments, the PVA has a molecular weight of about 15,000 to about 20,000.

Examples of suitable polyamide include those having an average molecular weight from about 10,000 to about 50,000. In some embodiments, the polyamide has an average molecular weight of about 10,000 to about 30,000, about 12,000 to about 30,000, about 10,000 to about 20,000, or about 12,000 to about 20,000. In further embodiments, the polyamide has a molecular weight of about 15,000 to about 20,000.

The mass ratio of the metal core to the first polymer can be about 1:0.25 to about 1:4, such as for example, about 1:0.25 to about 1:0.5, about 1:0.5 to about 1:1, about 1:1 to about 1:2, about 1:2 to about 1:3, about 1:0.5 to about 1:3, about 1:0.5 to about 1:2, or about 1:1 to about 1:3. Further examples of suitable mass ratios of metal core to first polymer include about 1:0.4 to about 1:0.6, about 1:0.9 to about 1:1.1, about 1:1.9 to about 1:2.1, or about 1:2.9 to about 1:3.0.

The mass ratio of the metal core to the second polymer can be about 1:2 to about 1:4. In certain embodiments the mass ratio of the metal core to the second polymer is about 1:3 to about 1:4, about 1:3.1 to about 1:3.9, about 1:3.2 to about 1:3.8, about 1:3.3 to about 1:3.8, about 1:3.4 to about 1:3.8, about 1:3.5 to about 1:3.8, or about 1:3.5 to about 1:3.7.

The mass ratio of the metal core to the first polymer to the second polymer can be about 1:0.25:3 to about 1:4:4, such as for example, about 1:0.25:3.6 to about 1:0.5:3.6, about 1:0.5:3.6 to about 1:1:3.6, about 1:1:3.6 to about 1:2:3.6, about 1:2:3.6 to about 1:3:3.6, about 1:0.5:3.6 to about 1:3:3.6, about 1:0.5:3.6 to about 1:2:3.6, or about 1:1:3.6 to about 1:3:3.6. Further examples of suitable mass ratios of metal core to first polymer to the second polymer include about 1:0.4:3.6 to about 1:0.6:3.6, about 1:0.9:3.6 to about 1:1.1:3.6, about 1:1.9:3.6 to about 1:2.1:3.6, or about 1:2.9:3.6 to about 1:3.0:3.6.

It has been advantageously discovered that by careful selection of the mass ratio of the metal core to the first polymer to the second polymer that long term stability of the nanoparticle can be improved, which inhibits agglomeration of the nanoparticle during storage.

The stability of the nanoparticle can be determined by measuring the rate and amount of nanoparticle agglomeration during storage. Agglomeration can be determined qualitatively by visual observation or by periodic light scattering tests on the test samples.

The polymer shell coated on the surface of the metal core can act as a protective layer and also to prolong the half-life of the nanoparticles in the patient's body (circulation half-life and/or local half-life).

The average hydrodynamic diameter of the nanoparticle can be about 10 nm to about 300 nm. For example, the average hydrodynamic diameter of the nanoparticle can be about 10 nm to about 250 nm, about 10 nm to about 200 nm, about 10 nm to about 150 nm, about 10 nm to about 100 nm, about 50 nm to about 100 nm, about 60 nm to about 100 nm, about 70 nm to about 100 nm, about 70 nm to about 90, or about 80 nm to about 90 nm. In certain embodiments, the average hydrodynamic diameter of the nanoparticle is less than about 20 nm, less than about 30 nm, less than about 40 nm, less than about 50 nm, less than about 50, less than about 60 nm, less than about 70 nm, less than about 80 nm, less than about 90 nm, or less than about 100 nm.

The nanoparticles can be prepared using any method known in the art. Depending on the properties of the synthons of the nanoparticles described herein, different techniques can be employed to efficiently prepare the nanoparticle. In certain embodiments, the nanoparticle is prepared using flash nanoprecipitation. For example, the iron (III)curcumin salt is barely soluble in water due to the hydrophobic nature of curcumin. In order to enhance its aqueous solubility, blood circulation time and prevent non-specific uptake by immune system, the iron-curcumin complex was further encapsulated inside polymeric micelle. PEG-PLA and iron-curcumin complex were dissolved in organic phase (e.g., DMF or acetone) while co-stabilizer PVP was dispersed in aqueous phase. Both streams were co-injected into a multi-inlet vortex mixer (MIVM), the PLA tail of PEG-PLA co-block polymer can adhere to the iron-curcumin complex surface and form micelle structure. PVP then forms a coating around the first polymer coating on the metal core by forming favorable interactions with the PEG groups on the PEG-PLA.

Due to the high energy generated during the rapid mixing in the MIVM, the nanoparticles were separated and prevented from aggregations. FIG. 7 shows the size and polydispersity index of the iron-curcumin complex nanoparticles prepared by MIVM.

In an alternative method, encapsulation of the metal core described herein in the polymer shell is accomplished by flash nano-precipitation using T-joint mixer instead of MIVM. By utilizing a T-joint mixer the number of steps to prepare the nanoparticle can be reduced and a lower injection rate can be used as compared with MIVM. When using MIVM to carry out flash nano-precipitation, four inlet streams are required. For example, two of the four inlet streams can be deionized water, one can be an organic solvent (containing curcumin and polymers), and one can be PVP with water. The injection rate (organic stream vs PVP stream) used can be 5.45 ml/min. Also, a higher concentration of PVP is required when using MIVM. In contrast, using T-joint mixer to carry out flash nano-precipitation of the present nanoparticles only requires two inlet streams including an organic and aqueous phases, wherein the organic phase is used to deliver the metal core and the polymers for encapsulating the metal core; the second inlet is an aqueous solution of PVP. When using the same injection rate at the MIVM method (5.45 ml/min), the T-joint mixer method requires only one tenth the concentration of PVP in the aqueous phase in order to result in nanoparticles with comparable PDI and particle size to nanoparticles prepared by using MIVM. In addition, using a T-joint mixer to carry out flash nano-precipitation is suitable for large-scale production and higher yield of the end product (the encapsulated nanoparticles).

Before flash nano-precipitation, the metal core must first be prepared. In cases where the metal core comprises a metal curcumin salt, the method comprises: pre-dissolving a paramagnetic transition metal compound into a small amount of an organic solvent to form a metal-containing solvent. The metal-containing solvent can then be added dropwise to a solution containing curcumin with stirring to form a deep red mixture, which can be continuously stirred under darkness at room temperature overnight. The reaction mixture is then lyophilized to form a powder. The power is then washed with water and a small amount of organic solvent before use, storage or further processing.

In certain embodiments, the organic solvent for pre-dissolving the metal core to form the metal-containing solvent and that for washing the powders after said lyophilization are the same organic solvent, which is dimethylformamide (DMF).

The core-shell structure composed of a zero valent metal core and a metal oxide shell can be synthesized in an aqueous environment as laid out below. The metal is dissolved into degassed water to form a metal-containing solution. A reducing agent is dissolved into degassed water with vigorous stirring and continuous $N_2$ purging to form a reducing agent solution and adding the metal-containing solution dropwise into the reducing agent solution, which forms a precipitate. The resulting mixture is continuously stirred after the addition of metal-containing solution until precipitation stops. The precipitate is then collected by sedimentation and washed with water three times followed by ethanol once. The solid is then dried under vacuum oven at 60° C. overnight. The metal oxide core spontaneously forms when the metal core is exposed to oxygen, which oxidizes the upper layer of the metal core thereby forming the core-shell structure.

In certain embodiments, the zero valent metal core is zero valent iron (Fe(0)) core and said metal oxide shell is $Fe_3O_4$. The core-shell structure can therefore be represented by Fe(0)@$Fe_3O_4$. In another embodiment, the metal compound being dissolved into $N_2$ purged water to form a metal-containing solution is iron(III) chloride ($FeCl_3$), thereby forming iron-containing solution. Excess reducing agent, such as $NaBH_4$ at 5 eq. in molar ratio with respect to iron, can be added to a degassed aqueous solution. The iron(III) chloride solution is added dropwise to the reducing solution under an inert atmosphere. After the addition of the metal-containing solution dropwise into the reducing agent solution, the mixture is continuously stirred for about 10 minutes until all metals are complety reduced by the reducing agent. In certain embodiments, the mixture is continuously stirred for an additional 10 minutes until the iron in the iron-containing solution is completed reduced by $NaBH_4$ into zero valent iron, which can be observed by the formation of black precipitates in a two-necked round bottom flask where the reduction of the iron takes place. Sedimentation of the synthesized zero valent iron can be assisted by using a magnet. The metal oxide shell is formed naturally on each of the zero valent iron cores due to oxidation, which occurs when the metal is exposed to oxygen. The complete oxidation of the zero iron metal core is inhibited by the protective coating of iron oxide that forms on the surface of the nanoparticle and stops oxygen from penetrating below the iron oxide shell.

The core-shell structure composed of a zero valent metal core and a metal oxide shell is further conjugated with curcumins by suspending the powders containing the core-shell structure into an organic solvent with vigorous stirring under an inert atmosphere before adding curcumins into the suspension. After adding curcumins into the suspension of the core-shell structure, the mixture is stirred under darkness at room temperature overnight to form a curcumin-conjugated core-shell structure nano-suspension. Organic solvent remaining in the nano-suspension is removed before drying. Drying of the nano-suspension can be achieved by adding a cryogenic protectant into the nano-suspension prior to freeze-drying. After freeze-drying, nanoparticles of the curcumin-conjugated core-shell structure are formed.

In certain embodiments, the cryogenic protectant comprises sucrose, mannitol, beta cyclodextrin, or glucose.

Also provided herein are pharmaceutical compositions comprising the nanoparticles described herein and at least one pharmaceutically acceptable excipient.

The pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils can be employed as a solvent or suspending medium. For this purpose, any fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, for example in their polyoxyethylated versions. These oil solutions or suspensions may also contain a long-chain alcohol diluent or dispersant, such as ethanol or similar alcohol.

The compounds and pharmaceutical compositions of the present invention may be administered orally, parenterally, by inhalation spray, topically, rectally, nasally, buccally, vaginally or via an implanted reservoir in dosage formulations containing The term "parenteral" as used herein includes subcutaneous, intravenous, intramuscular, intra-articular, intra-synovial, intrasternal, intrathecal, intrahepatic, intralesional and intracranial injection or infusion techniques.

The nanoparticles described herein are useful as diagnostics for various disease states using MRI including, but not limited to Alzheimer's disease, Huntington's disease, mad cow disease, multiple sclerosis, Parkinson's disease, Lewy Body disease, and stroke.

EXAMPLES

Example 1

Synthesis and Characterization of Metal-curcumin Complexes

Figure 1B:
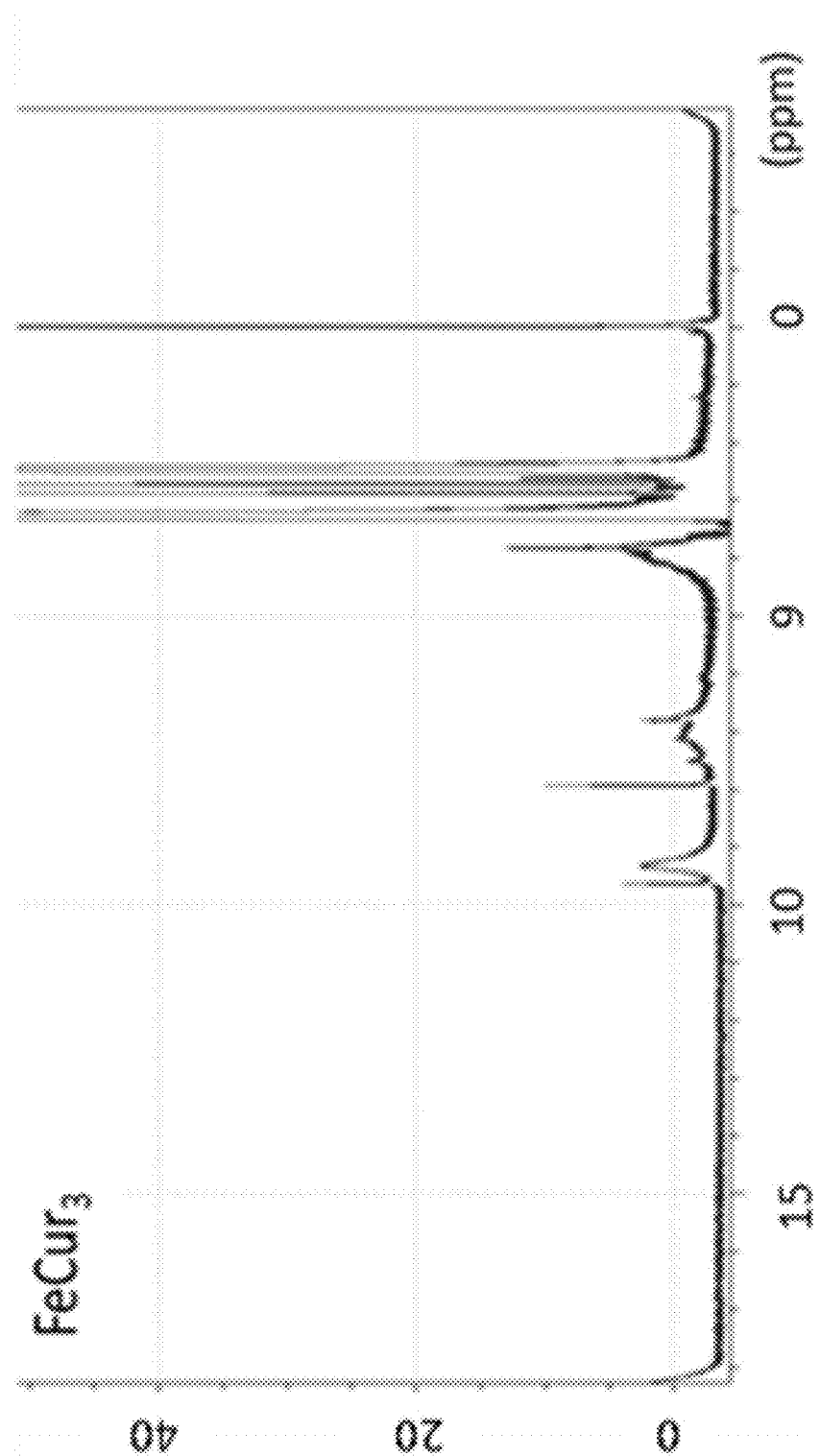
FIG. 1B shows the $^1$H-NMR of FeCur$_3$.
Figure 2:
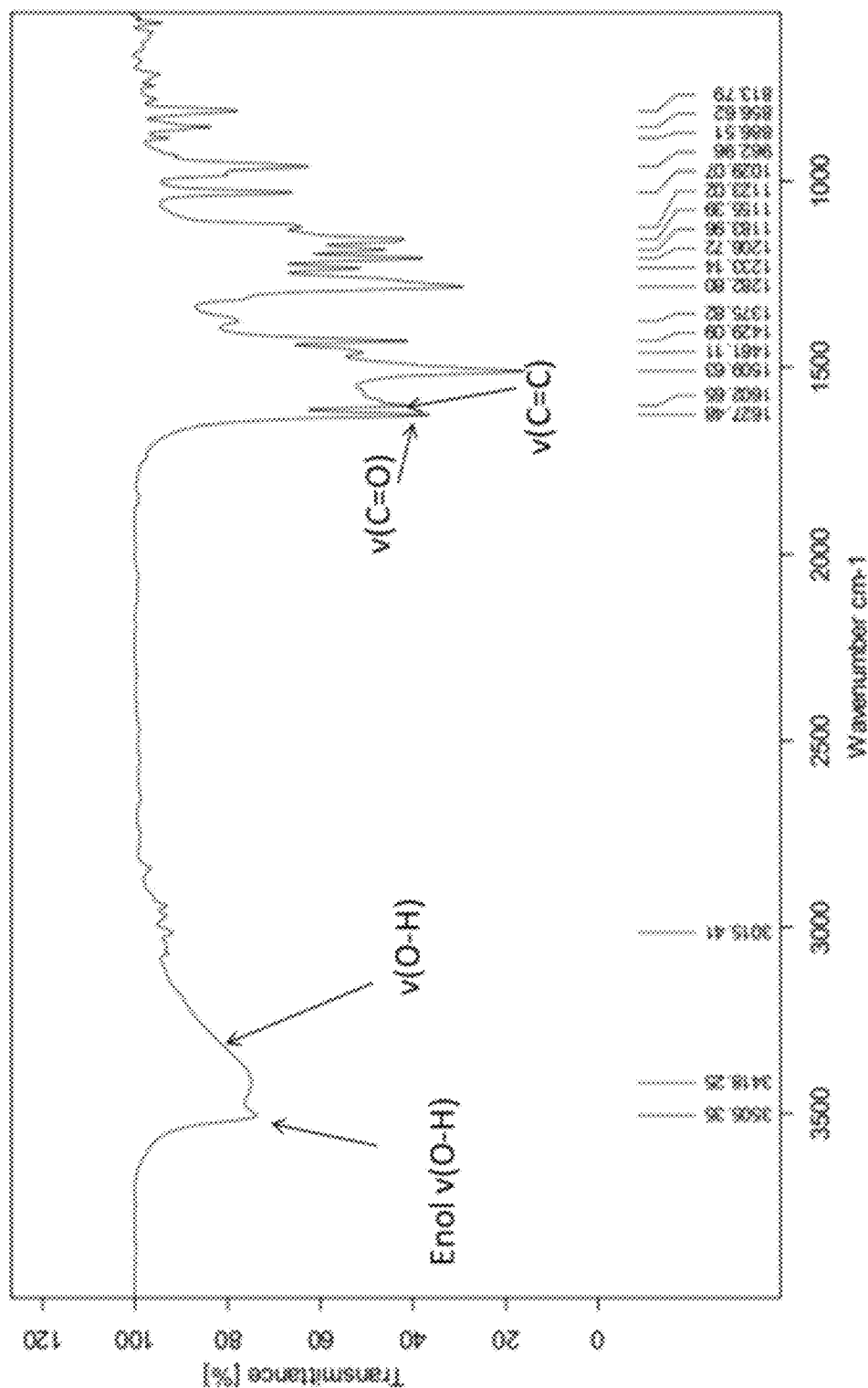
FIG. 2 shows the FTIR of curcumin.
Figure 3:
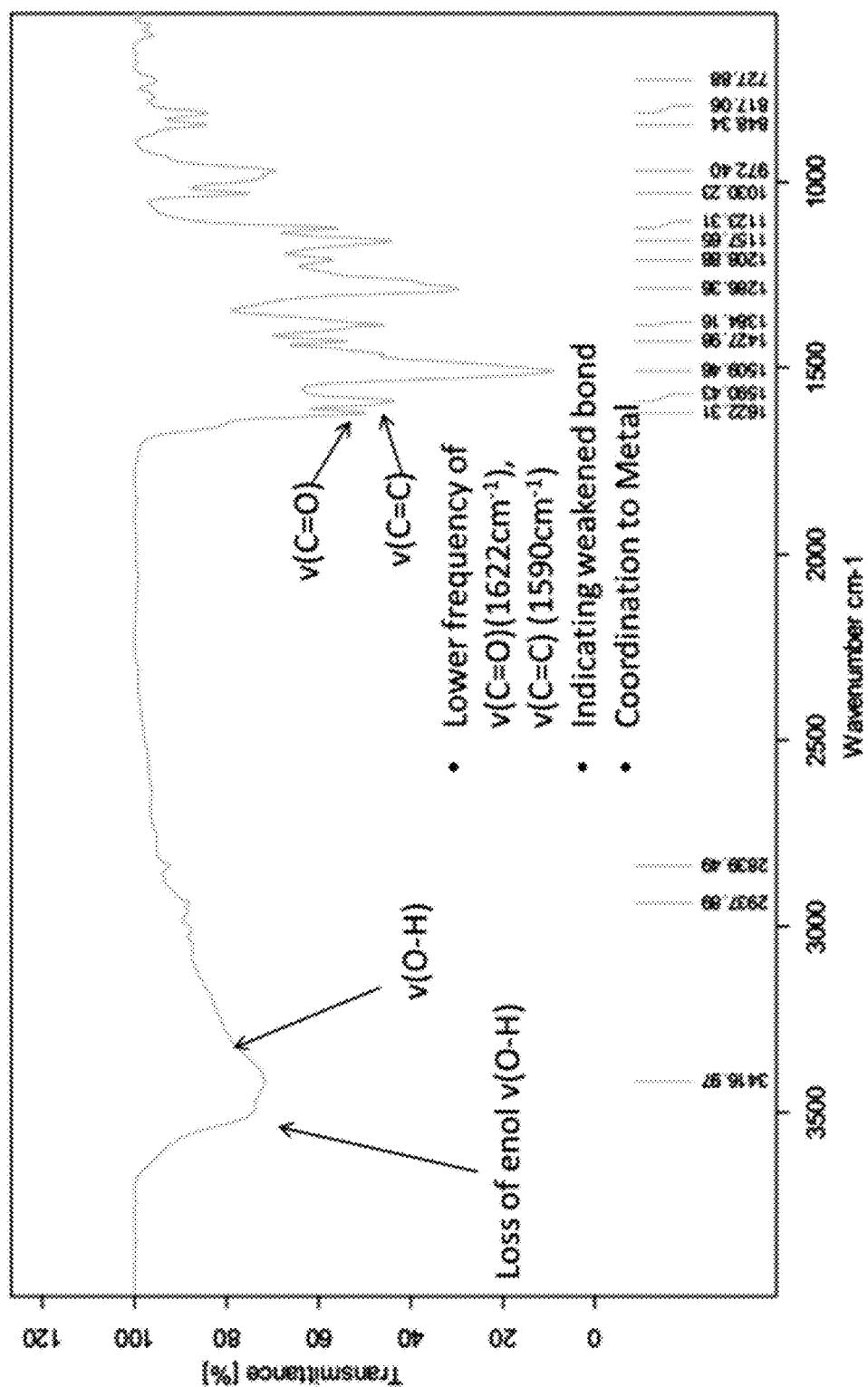
FIG. 3 shows the FTIR of FeCur$_3$.
Figure 4:
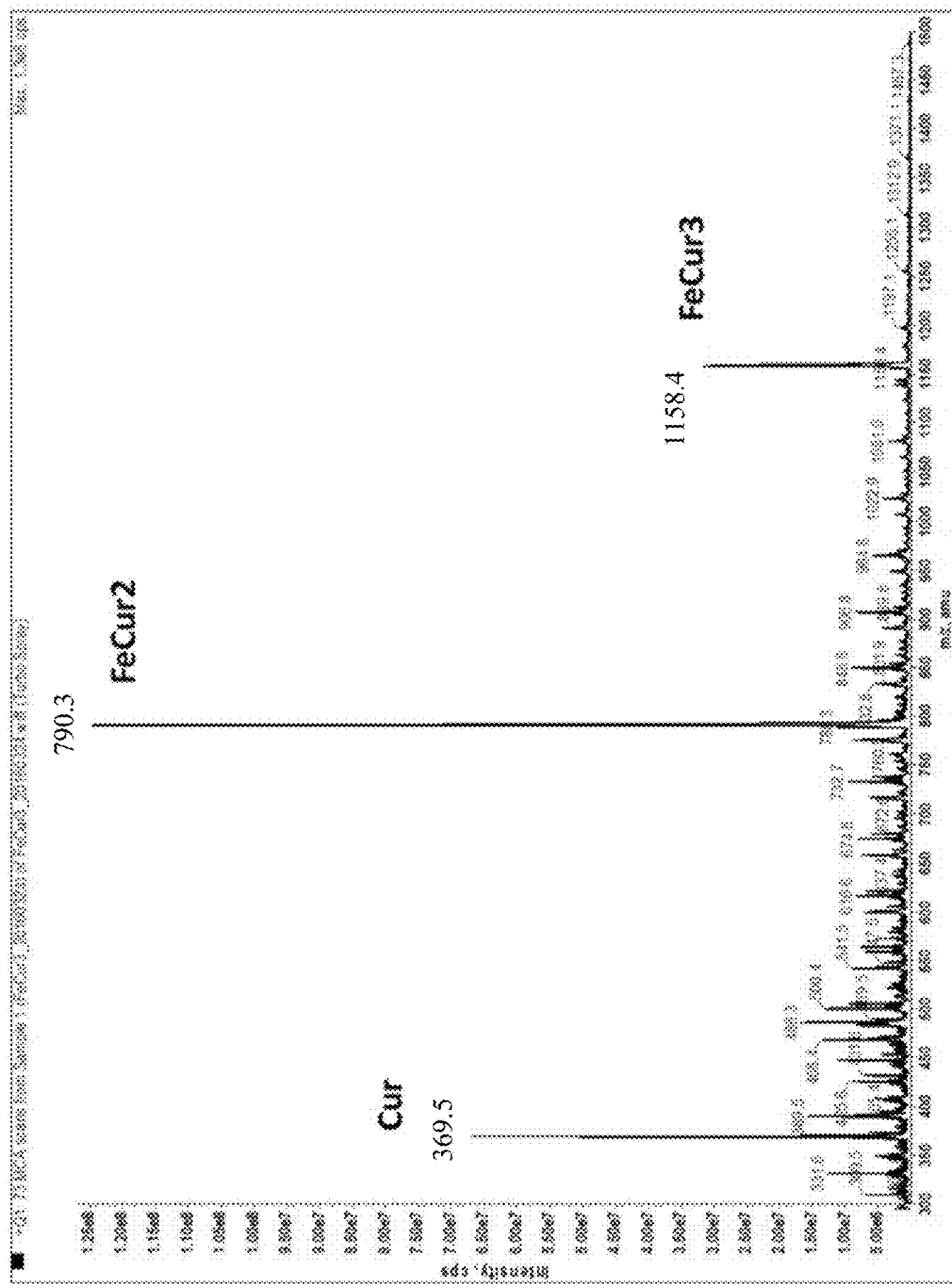
FIG. 4 shows the mass chromatogram of FeCur$_3$.
Figure 5:
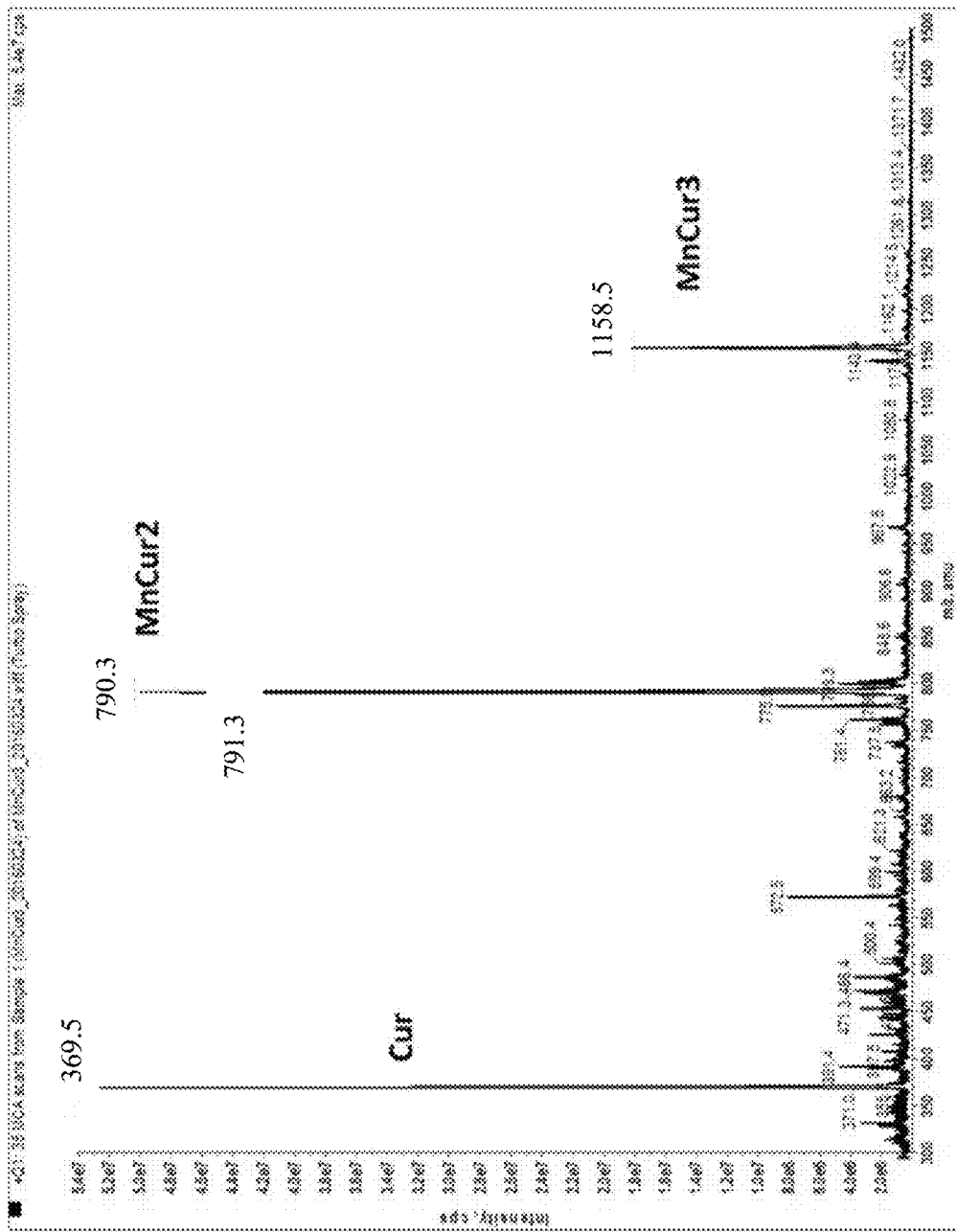
FIG. 5 shows the mass chromatogram of MnCur$_3$.
Figure 6:
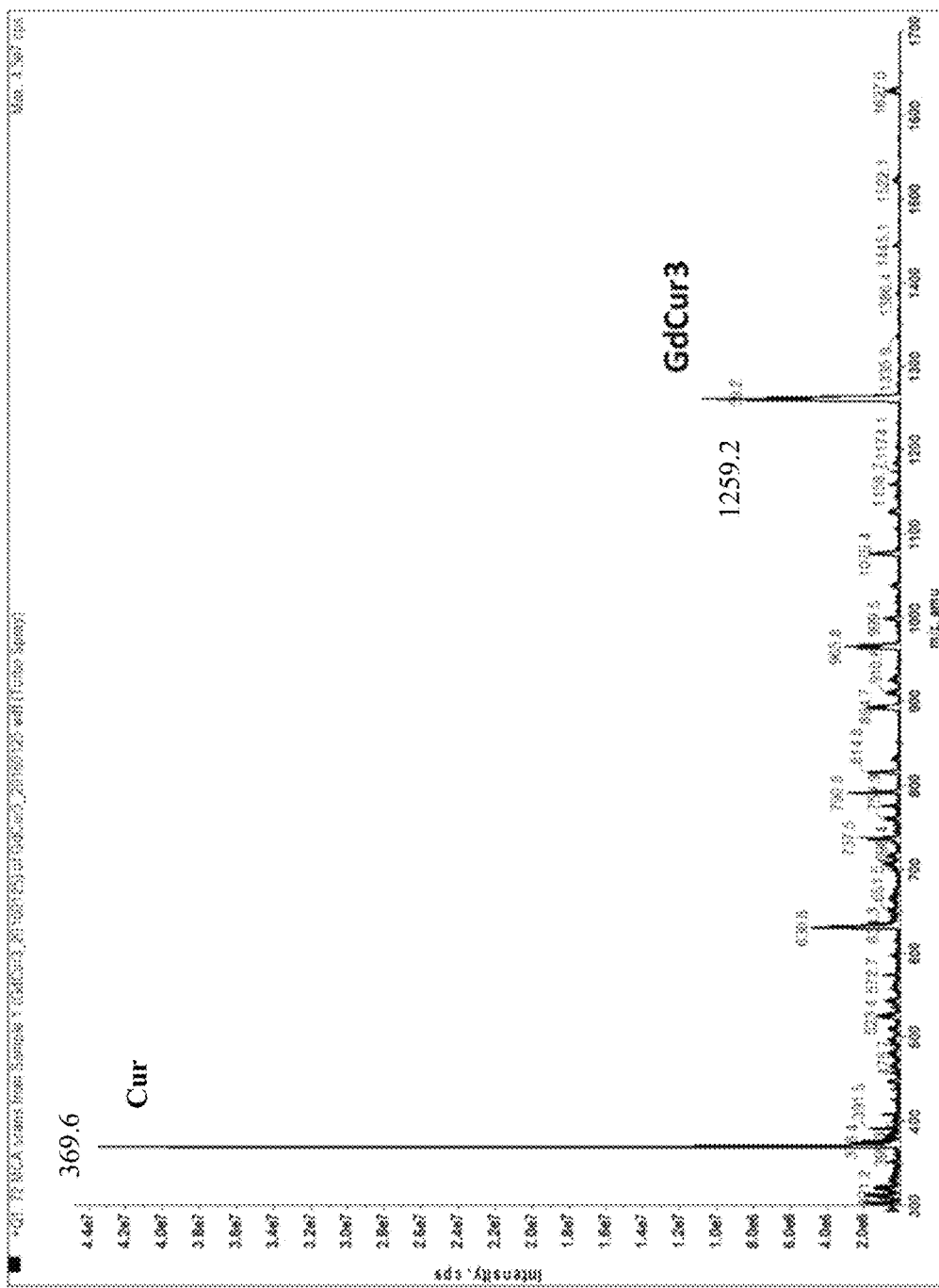
FIG. 6 shows the mass chromatogram of GdCur$_3$.

The synthetic strategy is similar to the reported literature (Sigurdsson et al., 2008; Wadghiri et al., 2003) with modification. Iron-curcumin complex will be described as an example for the synthetic procedure. Iron-curcumin complex was synthesized by dissolving curcumin with minimal amount of dimethylformamide. The iron solution (e.g., Fe(NO_3)_3 or $FeCl_3$) with one-third mole ratio of curcumin was pre-dissolved in dimethylformamide and added dropwise to the curcumin solution with stirring. The solution was turned to deep red and stirred for overnight under darkness at room temperature. The solution was lyophilized and the powder was washed with Milli-Q water and minimal amount of dichloromethane. FIG. 1 shows the 1H-NMR spectrum of iron-curcumin complex showed broad peaks of curcumin demonstrated the conjugated curcumin to the paramagnetic iron. The lower frequency of the C=O and C=C bond observed in the metal complex (compared to that of curcumin) in IR spectrum also showed the conjugation of curcumin to iron through the keto group (FIGS. 2 and 3). The mass spectra of iron-, manganese- and gadolinium-curcumin complex were shown (FIGS. 4 to 6) to demonstrate the feasibility of the synthetic strategy to broad spectrum of transition metals.

Example 2

Encapsulation of Iron-curcumin Complex by Flash Nano-precipitation (FNP) Method—MIVM The synthesized iron-curcumin complex is barely soluble in water due the hydrophobic nature of curcumin. In order to enhance its aqueous solubility, blood circulation time and prevent non-specific uptake by immune system, the iron-curcumin complex was further encapsulated inside polymeric micelle. PEG(2 k amu)-PLA (10 k amu) co-block polymer and iron-curcumin complex were dissolved in organic phase (e.g., DMF or acetone) while co-stabilizer polyvinyl pyrrolidone (PVP) (30 k amu) was dispersed in aqueous phase. The injection ratio is iron-curcumin complex: coblock polymer: PVP=1:2:4. Both streams were co-injected into Multi-inlet vortex mixer (MIVM) with injection rate at 45 ml/min and 5 ml/min for aqueous phase and organic phase, respectively. The PLA tail of PEG-PLA co-block polymer was in favor to adhere on the iron-curcumin complex surface and formed micelle structure. Also, due to the high energy generated during the rapid mixing (Liu et al., 2008; Gavi et al., 2007), the nanoparticles were separated and prevented from aggregations. FIG. 7 shows the size and polydispersity index of the iron-curcumin complex nanoparticles prepared by MIVM.

Example 3

Figure 8:
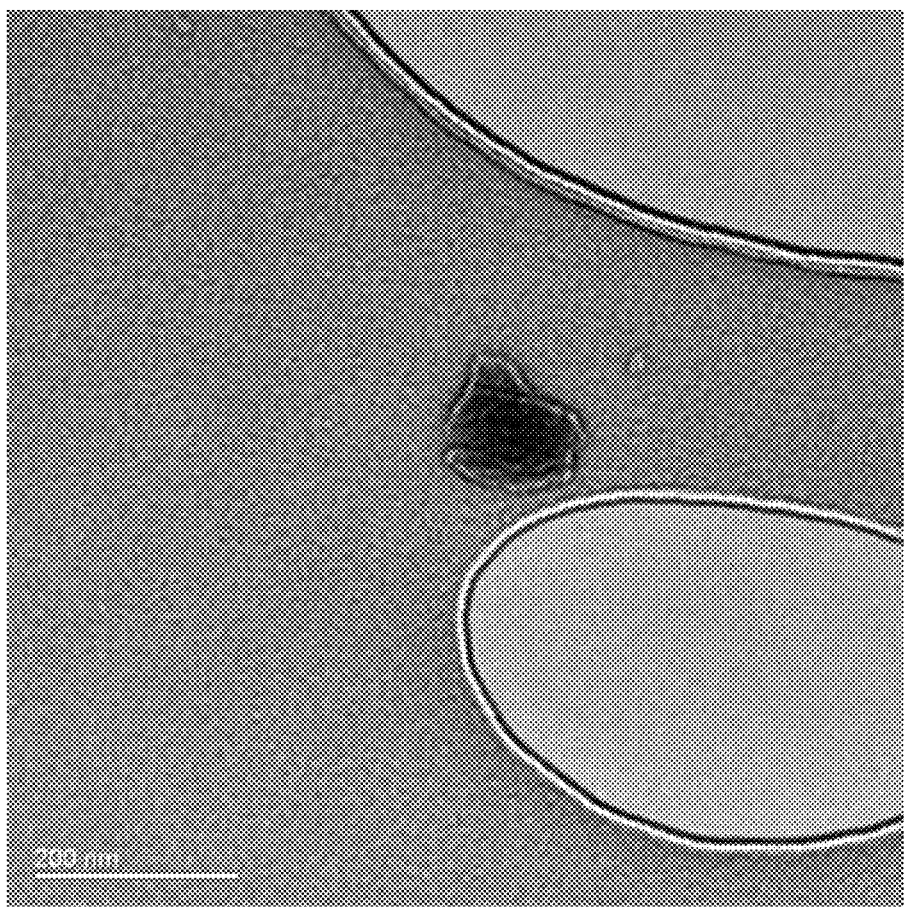
FIG. 8 shows a transmission electron microscopy image of a nanoparticle comprising a Fe(Cur)3 metal core with polymer shell comprising PEG (2K amu)-PLA(10 k amu) coblock polymer and PVP (30 k amu) in a molar ratio of metal core to PEG-PLA to PVP of 1:2:4.

Encapsulation of Iron-curcumin Complex by Flash Nanoprecipitation (FNP) Method—T-joint The synthesized iron-curcumin complex is barely soluble in water due to the hydrophobic nature of curcumin. In order to enhance its aqueous solubility, blood circulation time and prevent non-specific uptake by immune system, the iron-curcumin complex was further encapsulated inside polymeric micelle. Other than preparation by MIVM, T-joint was used for the nanoparticles preparation. PEG-PLA co-block polymer and iron-curcumin complex were dissolved in organic phase (e.g., DMF or acetone). For the T-joint setup, the organic phase with co-block polymer and metal complex and the aqueous phase were co-injected to the T-joint mixer. The nanoparticles were collected with 0.3% PVP aqueous solution with vigorous stirring. Due the high energy generated during the mixing, the nanoparticles were separated and prevented from aggregation. The size prepared by T-joint can reach (89.1±2.7) nm with PDI (0.21±0.01) (n=3) at the injection rate of 5/45 mL/min between the organic and the aqueous streams. FIG. 8 shows the transmission electronic microscope (TEM) image of the iron-curcumin complex nanoparticle encapsulated by PEG-PLA coblock polymer.

Although both MIVM and T-joint can facilitate the rapid mixing and resulting with similar particle size range, MIVM is suitable for small quantity of production and it is good for lower range of final concentration while T-joint is capable for continuous production and it can generate higher concentration of final production.

Example 3

Potential MRI Agent of Iron-curcumin Nanoparticles

Figure 9:
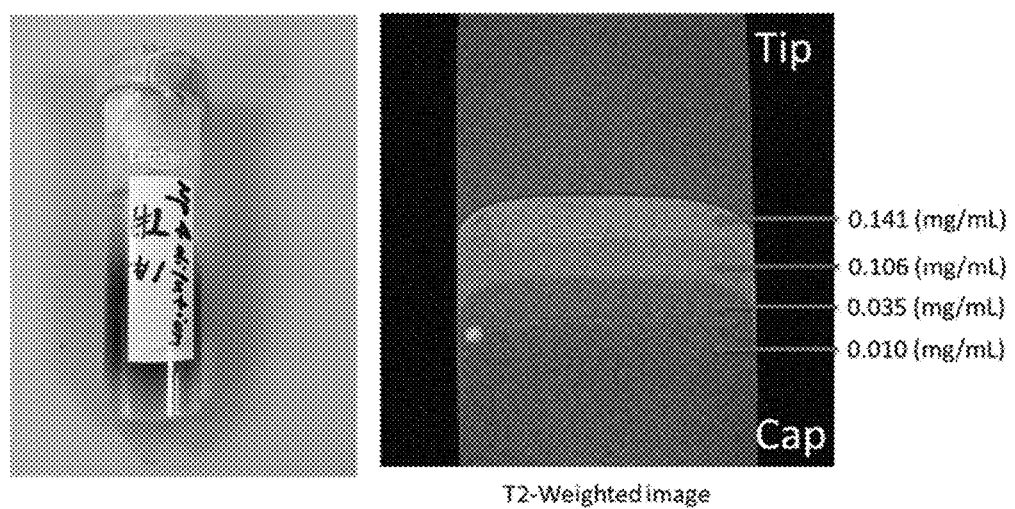
FIG. 9 shows the MRI signal of an agarose gel containing four layers having different concentrations (0.141 mg/ml, 0.106 mg/ml, 0.035 mg/ml, and 0.010 mg/ml) of a nanoparticle comprising a Fe(Cur)3 metal core with polymer shell comprising PEG (2K amu)-PLA(10 k amu) coblock polymer and PVP (30k amu) in a molar ratio of metal core to PEG-PLA to PVP of 1:2:4 described herein.
Figure 10A:
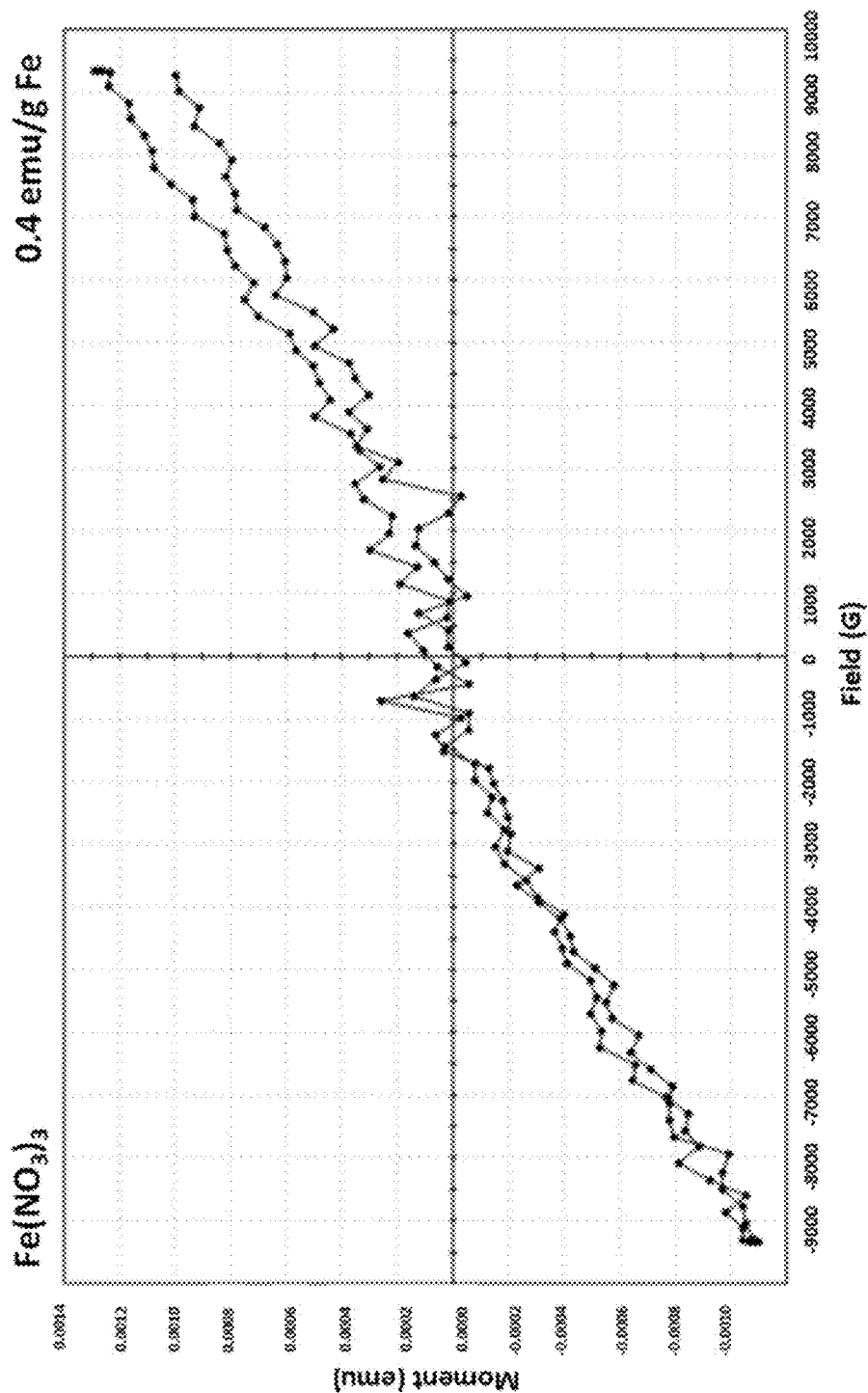
FIG. 10A shows the measured magnetic moment of Fe(NO$_3$)$_3$ (without polymer coating) by vibrating sample magnetometer.
Figure 10B:
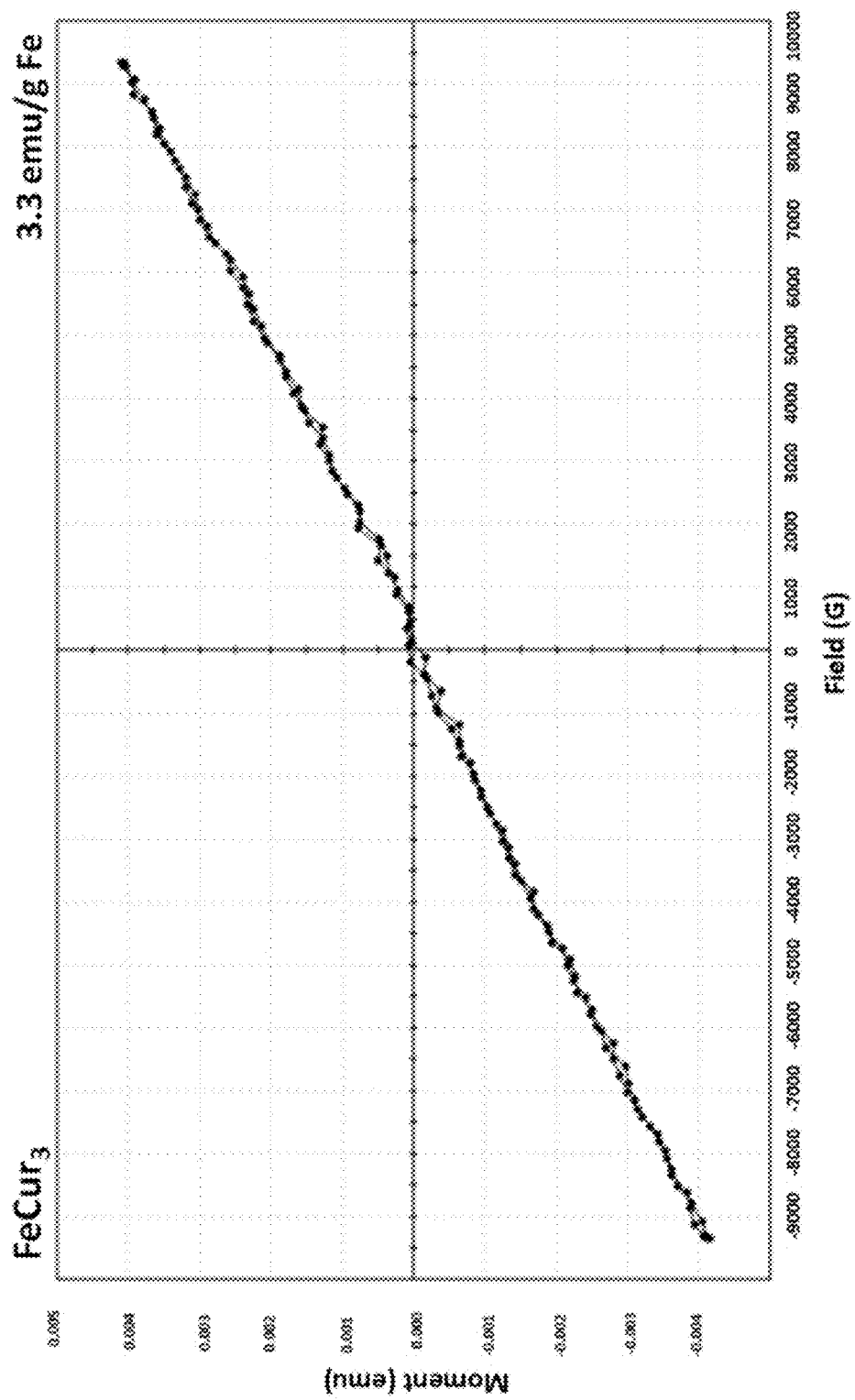
FIG. 10B shows the measured magnetic moment of FeCur$_3$ (without polymer coating) by vibrating sample magnetometer.

The potential of iron-curcumin nanoparticles to be a magnetic resonance imaging agent was investigated by scanning the MRI signal of iron-curcumin nanoparticles in agarose gel. Agarose gel with different concentration of iron-curcumin nanoparticles were prepared and stacked inside 50 mL centrifugal tube. It was then scanned by the Mill instrument to analyze the MRI signal (FIG. 9). The magnetic moment was also measured by vibrating sample magnetometer (FIG. 10A and FIG. 10B)

Example 4

Preparation of Zero Valent Iron

Iron (Fe) carries magnetic dipole moment, which is able to be detected under external magnetic field. Iron can present in different forms such as the zerovalent state (Fe(0) (zero valent iron "ZVI"), iron oxide ($Fe_xO_y$) and iron complexes ligated with different ligands (i.e., $FeCl_3$, $Fe(acac)_3$). Among them, ZVI possesses the strongest magnetic moment (up to 218 emu/g) followed by iron oxide (i.e., maghemite up to 80emu/g) and lastly the iron complexes.

Figure 11:
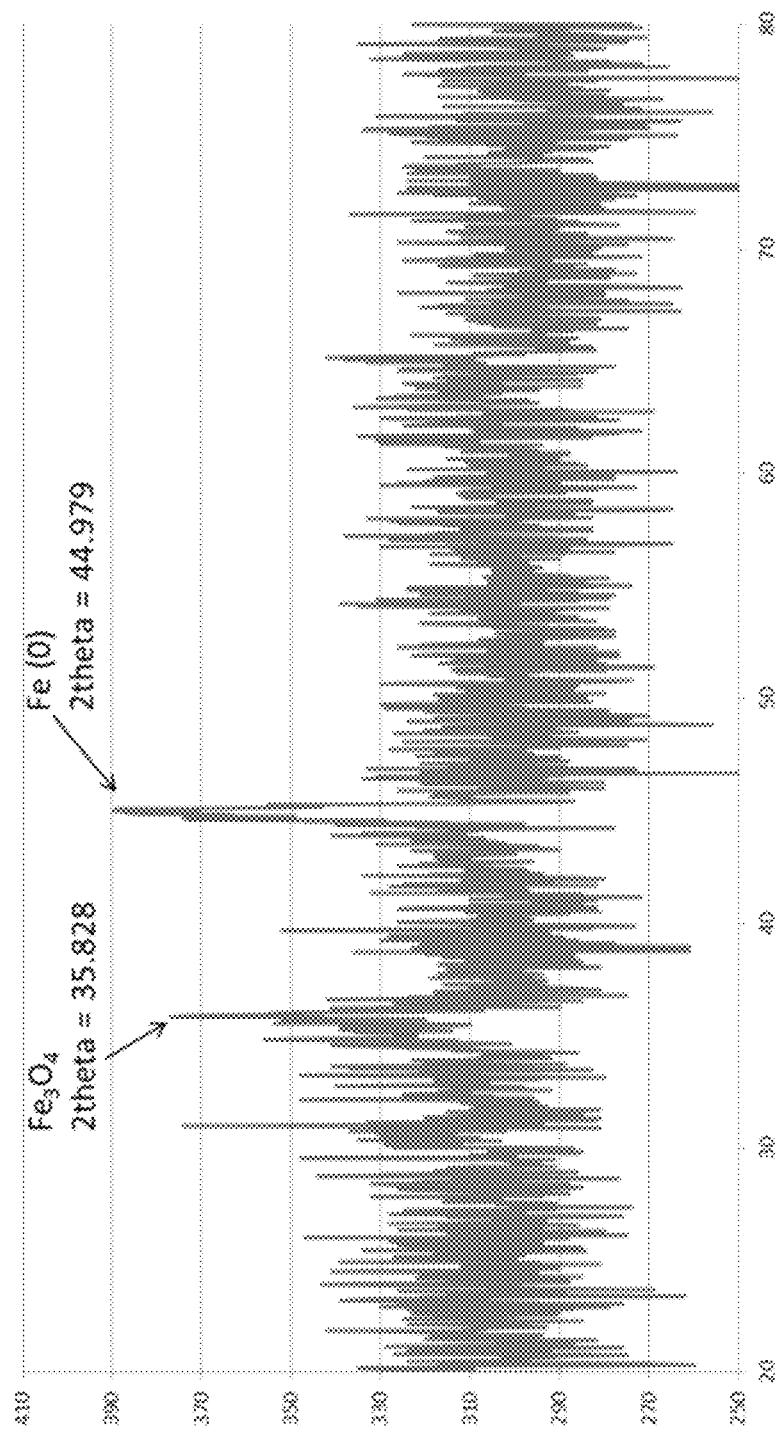
FIG. 11 shows the X-ray diffraction spectrum of Fe(0)@Fe$_3$O$_4$ core shell nanoparticle (without polymer coating).
Figure 12A:
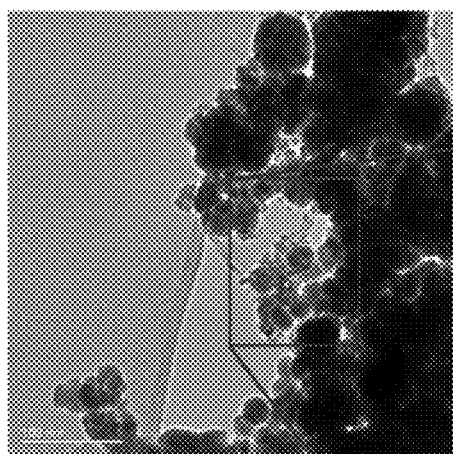
FIG. 12A shows transmission electron microscopy image showing the core-shell structure of Fe(0) coated with iron oxide (without polymer coating).
Figure 12B:
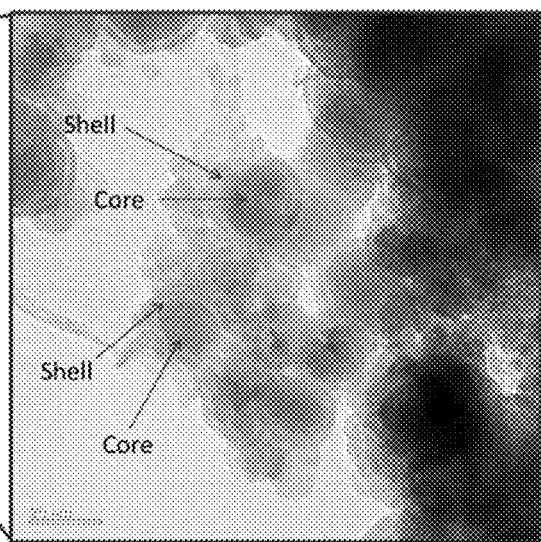
FIG. 12B shows a magnified view of a transmission electron microscopy image showing the core-shell structure of Fe(0) coated with iron oxide (without polymer coating).
Figure 13A:
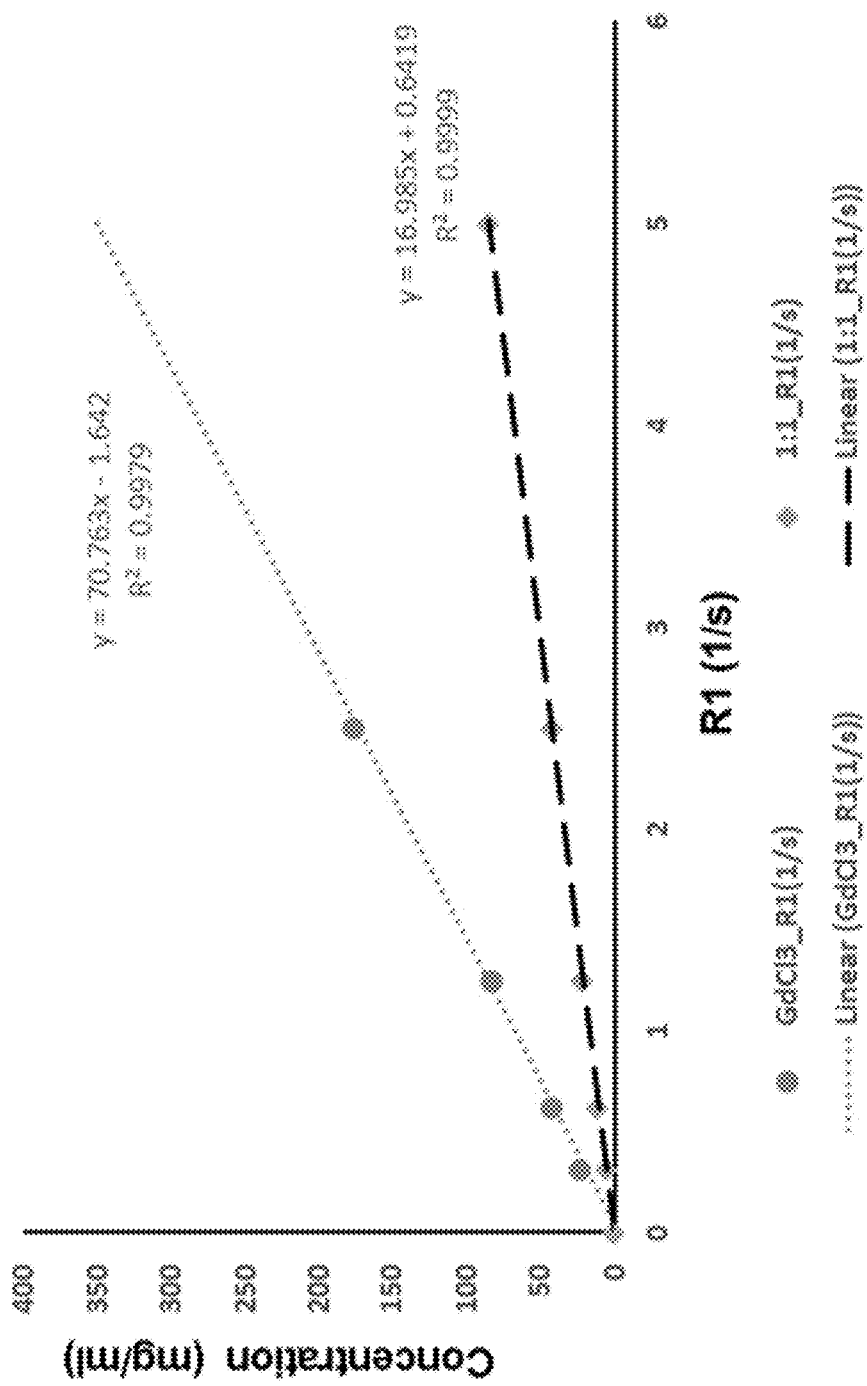
FIG. 13A shows the T1 relaxation of gadolinium chloride and iron curcumin complex.
Figure 13B:
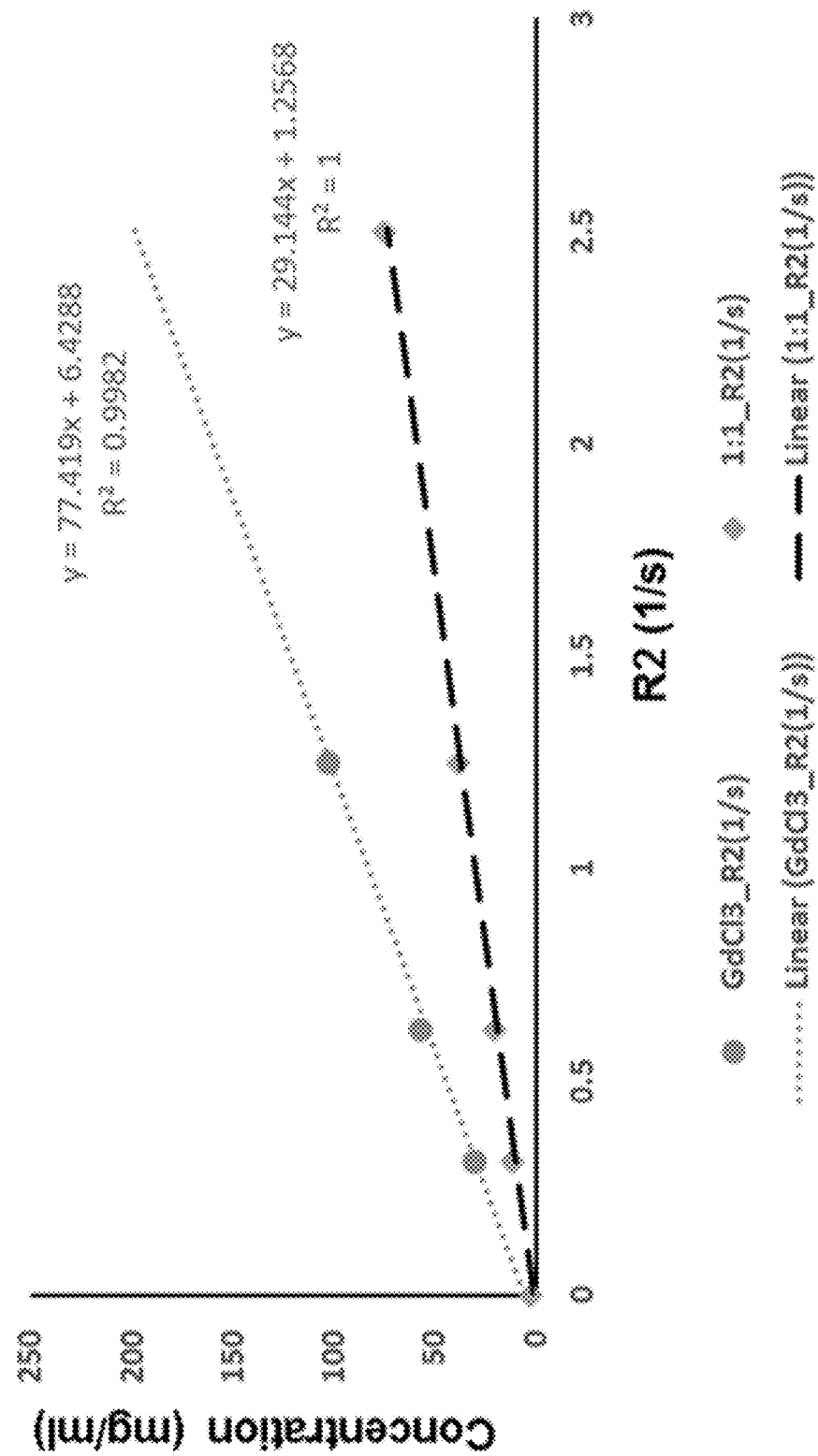
FIG. 13B shows the T2 relaxation of gadolinium chloride and iron curcumin complex.

The strength of the magnetic moment of different iron is proportional to the signal intensity measured under external magnetic field (i.e., diagnosis through MRI scanning). Therefore, ZVI diagnostic agent shows at least 2-fold increase compared to iron oxide. It results in following advantages in using ZVI over iron oxide in MRI scanning: 1) increase of signal-to-noise ratio so that the chance of false-positive diagnosis is reduced; 2) a more competent and powerful agent to be used for early diagnosis, even there is only small amount of pathogenic body; 3) reduction of diagnostic agent used so that patients' cost can be reduced and 4) reduce the amount of xenobiotics entering the patient's body; 5) reduction of the instrumental cost (such as MRI machine) because less powerful external magnetic field is enough for diagnosis The zero valent iron can be synthesized by reacting iron chloride solution with reducing agents such as $NaBH_4$ in aqueous [6]. Iron solution was prepared by dissolving iron chloride into $N_2$ purged Milli-Q water. Excess $NaBH_4$ (5 eq in mole ratio with respect to iron) was dissolved in $N_2$ purged Milli-Q water in a two-necked round bottom flask with vigorous stirring and with continuous $N_2$ purging. The iron solution was added dropwise into the $NaBH_4$ solution and black precipitate was immediately observed. Additional ten-minute stirring was given after all iron solution was added to ensure complete reduction of iron into zero valent iron. A magnet was used to help sedimentation of the zero valent iron nanoparticles. The zero valent iron nanoparticles was washed with $N_2$ purged Milli-Q water three times and absolute ethanol once. The powder was dried under vacuum oven at 60° C. overnight. XRD spectrum (FIG. 11) was shown to demonstrate the presence of zero valent iron. The TEM image (FIG. 12) shows the core-shell structure of zero valent iron coated with a layer of iron oxide.

Example 5

Preparation of Curcumin Coated Zero Valent Iron

Following Example 4, in order to increase the MRI signal during measurement, zero valent iron was used to be the magnetic core for the diagnostic agent. Zero valent iron was suspended in dimethylformamide with vigorous stirring under inert environment. Curcumin was then added to the suspension for coating purpose and it was then stirred overnight under darkness at room temperature.

The solvent remained in the nanoparticles suspension is eliminated by dialysis process. The dry process can be achieved by adding cryogenic protectant such as sucrose, mannitol, beta cyclodextrin and glucose then co-freeze with the nanosuspension prior for freeze drying. The dried nanoparticles can be re-suspended in aqueous. In order to enhance the blood brain barrier penetration abilities of the nanoparticles, polysorbate 80 or mannitol (Ren et al., 2009; Sun et al., 2004) is added to the reconstituted solution before applies in any in vivo testing.

Example 6

In vivo MRI Imaging for Alzheimer's Disease Detection

Figure 14:
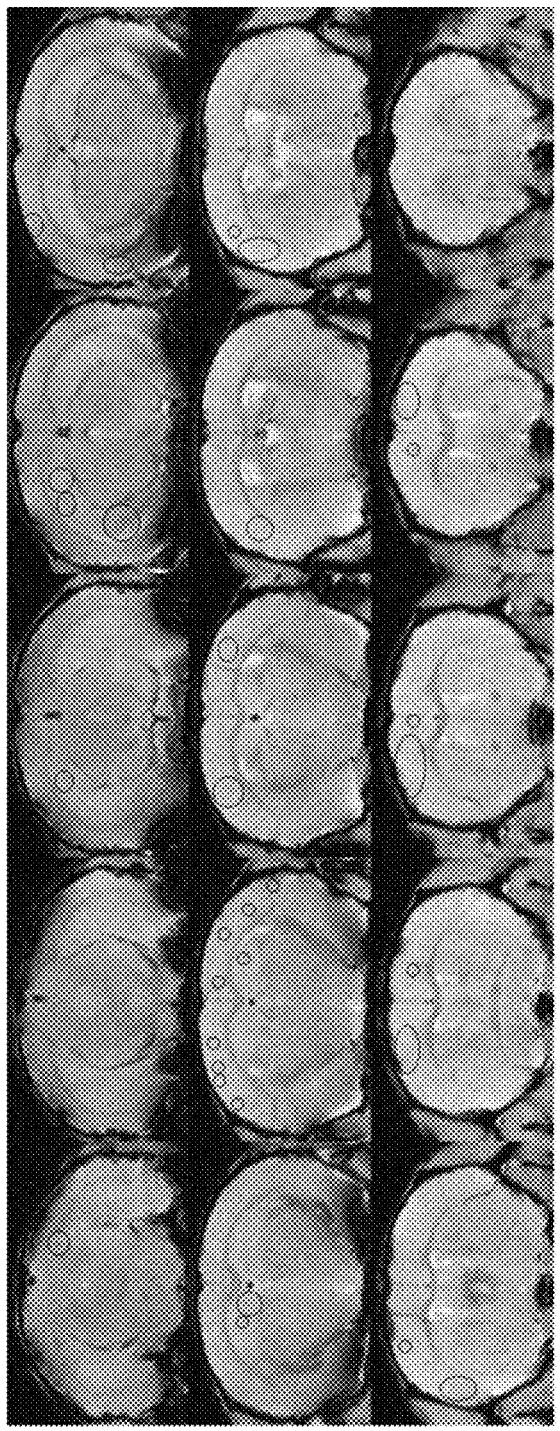
FIG. 14 shows in vivo MRI images of a 5×FAD transgenic mouse (age >6 months), which has been injected with a nanoparticle comprising a Fe(Cur)3 metal core with polymer shell comprising PEG (2K amu)-PLA(10 k amu) coblock polymer and PVP (30 k amu) in a molar ratio of metal core to PEG-PLA to PVP of 1:2:4 that have labeled amyloid beta plaques and highlighted by a black circle to better visualize the contrast.

The iron curcumin nanoparticle was injected in a transgenic mouse (genotype: 5×FAD) of >6 months old age. This type of transgenic mouse carries 5 human Alzheimer's disease genes and exhibits Alzheimer's disease pathology as early as 2 months old age. Examples of the serial in vivo MRI images of a rat brain from frontal to distal after 4 hours of iron curcumin nanoparticle injections was shown (FIG. 14). The amyloid beta plaques (hallmarks of Alzheimer's disease) were highlighted by the circles which were labeled by iron curcumin particles.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A nanoparticle comprising a metal core and a polymer shell coating the metal core, wherein the polymer shell comprises an inner shell comprising a first polymer and an outer shell comprising a second polymer, wherein the first polymer comprises a polyethylene glycol: polylactic acid coblock polymer (PEG-PLA) or a polyethylene glycol: poly(lactic-co-glycolic acid) coblock polymer (PEG:PLGA) and the second polymer is polyvinylpyrrolidone (PVP), polyvinyl alcohol (PVA), a polyamide, or a combination thereof and the mass ratio of the metal core to the first polymer to the second polymer is about 1:0.25:3 to about 1:4:4.

2. The nanoparticle of claim 1, wherein the metal core comprises Fe, Gd, Mn, Sn, Zn, Cu, Mg, or Pt.

3. The nanoparticle of claim 2, wherein the metal core comprises a metal flavonoid salt, a metal curcumonoid salt or a metal dye salt.

4. The nanoparticle of claim 3, wherein the metal curcumonoid salt comprises curcumin, demethoxycurcumin, or bismthoxycurcumin and the metal dye salt comprises di sodium 4-amino-3-[4-[4-(1-amino-4-sulfonato-naphthalen-2-yl)diazenylphenyl]phenyl]diazenyl-naphthalene-1-sulfonate, Thioflavin T, or Thioflavin S.

5. The nanoparticle of claim 2, wherein the metal core comprises Fe, Gd, Mn, or Sn.

6. The nanoparticle of claim 2, wherein the metal core comprises $FeO_3$, a core-shell $Fe(0)@Fe_3O_4$, or $Fe(Cur)_3$.

7. The nanoparticle of claim 1, wherein the first polymer is PEG-PLA comprising a polyethylene glycol block having an average molecular weight of 1,000 to 15,000 amu and a polylactic acid block having an average molecular weight of 1,000 to 15,000 amu.

8. The nanoparticle of claim 4, wherein the first polymer is PEG-PLA comprising a polyethylene glycol block having an average molecular weight of 1,000 to 3,000 amu and a polylactic acid block having an average molecular weight of 7,000 to 10,000 amu.

9. The nanoparticle of claim 1, wherein the first polymer is PEG:PLGA comprising a polyethylene glycol block having an average molecular weight of 1,000 to 15,000 amu and poly(lactic-co-glycolic acid) block having an average molecular weight of 1,000 to 15,000 amu.

10. The nanoparticle of claim 8, wherein the second polymer is PVP having an average molecular weight of 12,000 to 30,000.

11. The nanoparticle of claim 10, wherein the metal core comprises $Fe(Cur)_3$ and the mass ratio of the metal core to the first polymer to the second polymer is about 1:0.5:3.4 to about 1:3:3.8.

12. The nanoparticle of claim 11, wherein the first polymer is PEG-PLA comprising a polyethylene glycol block having an average molecular weight of 2,000 amu and a polylactic acid block having an average molecular weight of 10,000 amu.

13. The nanoparticle of claim 12, wherein the average hydrodynamic diameter of the nanoparticle is about 10 nm to about 300 nm.

14. A pharmaceutical composition comprising a diagnostically effective amount of a nanoparticle of claim 1 and at least one pharmaceutically acceptable excipient.

15. A method of performing a magnetic resonance imaging diagnostic procedure comprising the steps of:
   a. administering to a subject a diagnostically effective amount of a nanoparticle of claim 1; and
   b. exposing the subject to a magnetic resonance imaging procedure, thereby generating an image of at least a portion of the body of the subject.

16. The method of claim 15, wherein the nanoparticle comprises a metal flavonoid salt that binds to amyloid plaques in the subject.

17. The method of claim 15, further comprising the step of processing the image of at least a portion of the body of the subject to diagnose the presence or absence of Alzheimer's disease, Huntington's disease, mad cow disease, multiple sclerosis, Parkinson's disease, Lewy body dementia, or stroke.

18. The method of claim 16, wherein the at least a portion of the body of the subject comprises the brain.

19. The method of claim 15, wherein the subject is a human.

20. The method of claim 15, wherein the nanoparticle of claim 1 is administered parentally.

* * * * *